United States Patent [19] [11] Patent Number: 5,266,483
Iizuka et al. [45] Date of Patent: Nov. 30, 1993

[54] BACILLUS STRAIN AND INSECT PEST CONTROLLING AGENT

[75] Inventors: Toshihiko Iizuka, Sapporo; Michito Tagawa, Minamisaitama; Sachiko Yajima, Minamisaitama; Masao Kuwahara, Minamisaitama; Hiroshi Haruyama, Minamisaitama; Toshiyuki Umehara, Minamisaitama, all of Japan

[73] Assignee: Nissan Chemical Industries, Ltd., Tokyo, Japan

[21] Appl. No.: 911,570

[22] Filed: Jul. 9, 1992

[30] Foreign Application Priority Data

Jul. 9, 1991 [JP] Japan .................. 3-168435

[51] Int. Cl.$^5$ .............................. C12N 1/20
[52] U.S. Cl. .................. 435/252.5; 435/832
[58] Field of Search .......... 435/252.5, 832, 243; 424/405

[56] References Cited

PUBLICATIONS

I. T. Crawford et al., Journal of Microbiological Methods, 11 (1990), pp. 241-246.
H. Hofte et al., Microbiological Review, Jun. 1989, pp. 242-255.
I. T. Crawford et al., Journal of Microbiological Methods, 11 (1990) pp. 242-255.
A. H. Gharib et al., Journal of Econ. Entomol. 84(2) (Apr. 1991) pp. 436-439.
K. Frankenhuyzen et al., Appl. and Environmental Microbiology, (Jun. 1991) pp. 1650-1655.
B. E. Tabashnik et al., Journal of Econ. Entomol. 84(1) (Feb. 1991) pp. 49-55.
H. Hofte et al., Nucleic Acids Research, vol. 18 (1990), p. 5545.
J. A. Baum et al., Appl. and Environmental Microbiology, 56(11) (Nov. 1990), pp. 3420-3428.
W. J. Moar et al., Journal of Econ. Entomol. 82(6) (Dec. 1989), pp. 1593-1603.
M. Z. Haider et al., Gene, 52 (1987), pp. 285-290.
L. Thorne et al., Journal of Bacteriology, vol. 166 (3), (Jun. 1986), pp. 801-811.
L. Masson et al., American Chemical Society, (1990) pp. 61-69.
W. Chungjatupornchai et al., Eur. J. Biochem. 173, (1990) pp. 9-16.
W. Ahmad et al., FEMS Microbiology Letters 59 (1989) pp. 197-201.

Primary Examiner—Douglas W. Robinson
Assistant Examiner—Deborah K. Ware
Attorney, Agent, or Firm—David G. Conlin; Ronald I. Eisenstein

[57] ABSTRACT

The present invention provides novel strains of *Bacillus thuringiensis* var. *Kurstaki*, No.145, No.116 and No.161.

These strains produce an insecticidal crystal toxin which is useful as an active component in a insect pest-controlling agent.

3 Claims, 1 Drawing Sheet

BACILLUS STRAIN AND INSECT PEST CONTROLLING AGENT

FIELD OF THE INVENTION

This invention relates to novel bacteria strains, particularly to novel *Bacillus thuringiensis* (which will be referred to hereinafter as "Bt") strains and application thereof.

The invention relates to the novel strains which produce an insecticidal crystal toxin. The toxin can control lepidopterous insect pests more effectively than commercially available agents. The lepidopterous insect pests cause serious damages to plants in a farming field, non-farming field and forest.

The invention further relates to an agent for controlling the lepidopterous insect pests, which comprises the novel strains or crystal toxin produced thereby.

BACKGROUND

Bt is a gram-positive bacilliform bacterium which produces a crystal protein at a sporulation stage in the end of a logarithmic growth phase. When an insect orally takes the crystal protein into a gastrointestinal tract, the crystal protein will be subjected to alkaline and enzymatic degradations in a digestive juice so as to show an insecticidal activity which causes an intestinal and systemic paresis The crystal protein is therefore referred to as "δ-endotoxin" (Heimpel, A. M.; Ann. Rev., Entomology 12, 287-322, 1967).

The crystal protein produced by Bt is generally of a form such as a diamond-shaped, bipyramidal and rhomboidal one. The crystal protein is formed with an endospore in a sporangium and released with it from the sporangium (Hannay, C. L.; Nature 172, 1004, 1953).

Bt has been classified on the basis of H-antigen according to the proposal by De Barjac and Bonefoi (Entomophaga 7, 5-31, 1962), and reported to have 24 subspecies (33 strains) including serotypes 1 to 23 and wuhanensis which has no H-antigen (Toshihiko Iizuka, Chemistry and Biology 27, 287-302, 1989). However, it was found that some different kinds of strains were present in the same serotype (Krywienczyk, J., et al; J. Invertebr. Pathol.; 31, 372-375, 1978, Iizuka, T., et al; J. Sericult. Sci. Japan; 50, 120-133, 1981).

The crystal protein produced by Bt is generally known to selectively show the insecticidal activity to the lepidopterous insects. Recently, subspecies have been found, which produce an irregular and cuboidal crystal protein beside a bipyramidal one (Yoshio Akiba; Jpn. J. Appl. Entomol. Zool., 30, 99-105, 1986, Ohba, M., et al; J. Invertebr. Pathol. 38, 307-309, 1981). Among them, there were reported strains which can show a strong insecticidal activity against a leaf beetle or a larva of a mosquito (Hall, I. M., et al; Mosquito news 37, No.2, 1977).

A crystal protein gene (CP gene) of Bt is usually encoded by a plural of somatic plasmid DNAs. The CP gene has been already cloned and its nucleotide sequence has been also determined in some subspecies (Toshihiko Iizuka, Chemistry and Biology 27, 287-302, 1989).

Further, many researches have been intensively conducted on introduction of such cloned CP genes into a plant body and some of them were reported to succeed, for example, in the case of tobacco (Vaeck, M., et al; Nature 328, 33-37, 1987). The CP gene coding for a crystal protein which shows a stronger insecticidal activity is now sincerely desired.

The lepidopterous insect pests having taken the crystal toxin produced by Bt will stop their feeding behavior several hours later and never do any harm to plants. Almost species of the lepidopterous insect pests will die of intoxication by the crystal toxin about 24 to 72 hours later. The intoxication will be sometimes accompanied by sepsis induced by the presence of spores. Thus, a main reason of the death is due to the crystal toxin which will function only after its dissolution in a bowel of the larva.

Due to such functional mechanism of the crystal toxic protein as well as the fact that the crystal toxin is an easily-degradable polypeptide, it is known that the crystal toxin does no damage to human, pet animals, birds, fishes and plants.

Accordingly, Bt or the crystal toxic protein produced thereby is very potential as a microbial pesticide which does not pollute an environment (BT agent), especially as an insecticide against the lepidopterous insect pests. One or more strains of Bt have been actually used for a long time as the insecticide in agriculture.

The strain of Bt which is most generally used as a commercial product is Bt var. kurstaki HD-1, which will be referred to hereinafter as "HD-1."

SUMMARY OF THE INVENTION

The present inventors have found novel strains of Bt. The new strains of the present invention are definitely distinguished from HD-1 by the fact that they show an improved insecticidal activity against a series of dipterous and lepidopterous insect pests but they show only a low insecticidal activity against a beneficial lepidoptera, *Bombyx mori*.

Accordingly, one object of the present invention is to provide novel strains of Bt var. Kurstaki, No.145, No.161 and No 116, which have been originally deposited at Fermentation Research Institute Agency of Industrial Science and Technology on Jun. 4, 1991 with Accession Numbers FERM P-12289, FERM P-12291 and FERM P-12290, respectively. These strains have been transferred from the original deposit to the deposit under Budapest Treaty conditions on Jun. 29, 1992 with new Accession Numbers FERM BP-3905, FERM BP-3906 and FERM BP-3907, respectively.

Another object of the present invention is to provide a novel insecticide composition or insect pest-controlling agent, which comprises as a main component an insecticidal crystal toxin produced by the novel strains No.145, No.116 and No.161 according to the present invention.

Yet another object of the present invention is to provide a method for the protection of a plant from damage caused by an insect pest, comprising feeding the insect pest with the insecticidal crystal toxin produced by the novel strains No.145, No.116 and No.161 according to the present invention or treating a plant with an insecticidally effective amount of the same toxin prior to or during suffering from the damage.

DETAILED DESCRIPTION OF THE INVENTION

Figure 1:
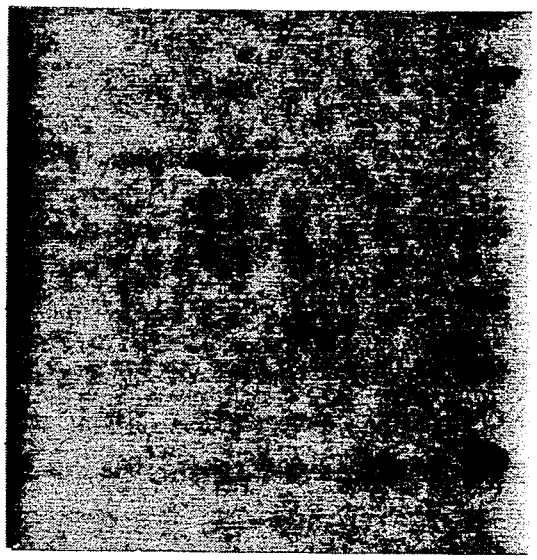
FIG. 1 shows a pattern on SDS-polyacrylamide gel electrophoresis of the proteins which were obtained by a trypsin treatment of the alkaline soluble protein of the strain No.116 (lane 1), No.145 (lane 2), No.161 (lane 3) and HD-1 (lane 4), respectively. Lane 5 is a pattern of trypsin and lane 6 shows migration markers.

The above three novel strains according to the present invention were isolated from soil in Hokkaido area and identified to have the following features.

Features of the strain No.145:

Colony Formation: A large colony which is typical for Bt, the surface of which looks dark and dull.

Cell morphology: A typical one for Bt.

Serotype of H-antigen: 3a3b3c, kurstaki.

Intracellular component: A sporulating cell produces a diamond-shaped crystal which sometimes contains a small cuboidal crystal.

Plasmid: A pattern of a plasmid of the strain on an agarose electrophoresis is clearly distinguished from that of the known strains such as Bt var. kurstaki HD-73 (which will be hereinafter referred to as "HD-73") and Bt var. kurstaki HD-63 (which will be hereinafter referred to as "HD-263").

Alkaline-soluble protein: The strain has the proteins which run to about 125,000 dalton and about 60,000 dalton on the electrophoresis.

Activity: The strain has an insecticidal activity which is from 5 to 100 times higher than the known HD-1 and commercially available Bt agents against all the lepidopterous insect pests tested, but has the insecticidal activity which is about 20 times lower than the known HD-1 and commercially available Bt agents against a beneficial lepidoptera, Bombyx mori. The strain also shows a stronger insecticidal activity than HD-1 against a dipterous insect pest, mosquito.

Features of the strain No.116:

Colony Formation: A large colony which is typical for Bt, the surface of which looks dark and dull.

Cell morphology: A typical one for Bt.

Serotype of H-antigen: 3a3b3c, kurstaki. Intracellular component: A sporulating cell produces a diamond-shaped crystal which sometimes contains a small cuboidal crystal.

Plasmid: A pattern of a plasmid of the strain on an agarose electrophoresis is clearly distinguished from that of the known strains such as HD-1, HD-73 and HD 263.

Alkaline-soluble protein: The strain has the proteins which run to about 130,000 dalton and about 60,000 dalton on the electrophoresis.

Activity: The strain has an insecticidal activity which is from 5 to 80 times higher than the known HD-1 and the commercially available Bt agents against all the lepidopterous insect pests tested. The strain also shows a similar insecticidal activity to Bt var. israelensis (which will be hereinafter referred to as "israelensis") against dipterous insect pest, mosquito. However, it has a lower insecticidal activity than the known HD-1 and the commercially available Bt agents against a beneficial lepidoptera, *Bombyx mori.*

Features of the strain No. 161:

Colony Formation: A large colony which is typical for Bt, the surface of which looks dark and dull.

Cell morphology: A typical one for Bt.

Serotype of H-antigen: 3a3b3c, kurstaki.

Intracellular component: A sporulating cell produces a diamond-shaped crystal which sometimes contains a small cuboidal crystal.

Plasmid: A pattern of a plasmid of the strain on an agarose electrophoresis is clearly distinguished from that of the known strains such as HD-1, HD-73 and HD-263.

Alkaline-soluble protein: The strain has the proteins which run to about 130,000 dalton and about 60,000 dalton on the electrophoresis.

Activity: The strain has an insecticidal activity which is from 2 to 50 times higher than the known HD-1 and commercially available Bt agents against all the lepidopterous insect pests tested. The strain also shows a stronger insecticidal activity than HD-1 against dipterous insect pest, mosquito. However, it has a lower insecticidal activity than the known HD-1 and the commercially available Bt agents against a beneficial lepidoptera, *Bombyx mori.*

These three strains produce the toxic proteins which are different from that of HD-1 in a digestion pattern by proteases and various digestive juices of insects. For example, 130 Kd protein of the toxic protein derived from HD-1 will be digested into a smaller molecule by trypsin. On the other hand, the corresponding proteins from the strains of the present invention are hardly digested by trypsin, and even if digested, a pattern on the electrophoresis of the resulting molecules is different from that of HD-1 (FIG. 1).

As seen from the above data, although the three novel strains are similar to the known HD-1 in view of morphological features, they are distinguished from the known strain, HD-1.

The strains, No.145, No.116 and No.161 can be cultured in a standard fermentation method and medium.

The medium may contain as carbon source sucrose, maltose, glucose, fructose, molasses, soluble starch and the like.

As nitrogen source, there may be mentioned ammonium sulfate, ammonium chloride, cottonseed powder, yeast extract, soybean cake, casein hydrolysate and the like.

Minerals and vitamins may be supplied by the above carbon or nitrogen sources, which may, however, be added separately.

The strains of the present invention are cultured preferably at pH of from 5 to 8 and a temperature of from 25 to 30° C. for 2 and 5 days. The culture is carried out preferably in a stirred and aerated system, a submerged culture in the same system being preferred in a mass-production.

The crystal toxic protein may be isolated and collected from a culture medium by a conventional manner such as centrifugation and filtration. Alternatively, the culture medium containing the strain per se and/or free crystal toxic protein may be concentrated or dried to give a powder by a conventional method such as a spray-drying, as long as the method does not deteriorate the toxic activity of the protein.

In case the resulting crystal toxin comprises viable cells, such cells will be sterilized in a conventional method such as heat treatment, ultrasonication, homogenation, physical treatment such as radiation, chemical treatment such as those with formalin, hydrogen peroxide, sulfite salts, chlorine compounds, β-propiolactone, surfactants, ethylene oxide, and propylene oxide and biological treatment such as autolysis, phage treatment and lysozyme treatment. From an industrial point of view, heat treatment, homogenation and chemical treatment are preferred. It is also noted that the treatment should not deteriorate the activity of the crystal toxic protein.

When the crystal toxin component according to the present invention is used in an insect pest-controlling agent, it may be mixed with a natural and mineral fiber such as talc and kaolin, a solid carrier such as a pumice stone, bentonite and diatomite, and a liquid carrier such as water, and optionally supplemented with an emulsifier, dispersant, suspensions, penetrating agent, spreader and stabilizer. The agent may be formulated for a practical use into any form such as a wettable powder, powder, granule, flowable agent.

The agent according to the present invention may be formulated or sprayed together with other agents such as herbicide, pesticide, fungicide, plant-growth regulator, synergist, attractant, plant-nutrient and fertilizer.

An application amount of the crystal toxin-containing material (active component) may be varied depending on an application place, time and method, pest insects to be treated and crop to be protected, the active component usually being 0.1-99%, preferably 0.5-50% by weight of the agent.

All parts, percentages and proportions referred to herein and claims are by weight unless otherwise indicated.

Examples of the amounts of each component in the agent of the present invention will be summarized as follows:

|  | active component | carriers | surfactant | (others auxiliary substance) |
|---|---|---|---|---|
| wettable powder | 1-70 | 15-93 | 3-10 | 0-5 |
| powder | 0.01-30 | 67-99.5 |  | 0-3 |
| granule | 0.01-30 | 67-99.5 |  | 0-8 |
| flowable agent | 1-70 | 10-90 | 1-20 | 0-10 |

When applied, a wettable powder and flowable agent are diluted with a predetermined amount of water, powder and granular agent may be directly applied without dilution.

Each component of the agent may be exemplified as follows:
Wettable powder
  active component: the crystal toxin-containing material according to the present invention;
  carriers calcium carbonate, kaolinite, Sieglite D, Sieglite PEP, diatomite, talc;
  surfactant calcium lignosulfonate, Solpol, Lunox;
  others Carplex #80.
Powder
  active component: the crystal toxin-containing material according to the present invention;
  carriers: calcium carbonate, kaolinite, Sieglite D, diatomite, talc;
  others: diisopropyl phosphate, Carplex #80.
Granule
  active component: the crystal toxin-containing material according to the present invention;
  carriers: wheat flour, wheat bran, corn grits, Sieglite D;
  others: paraffin, soybean oil.
Flowable agent
  active component: the crystal toxin-containing material according to the present invention;
  carriers: water;
  surfactant: Solpol, sodium lignosulfonate, Lunox, Nippol;
  others: ethyleneglycol, propyleneglycol.

The insect pest-controlling agent according to the present invention will be illustrated below with reference to the following unlimited formulation examples.

FORMULATION EXAMPLE 1: WETTABLE POWDER

| | |
|---|---|
| the crystal toxin-containing material according to the present invention | 25 parts |
| Sieglite PEP (a trade name of mixture of kaolinite and sericite; manufactured by Sieglite Industry Co.) | 66 parts |
| Solpol 5039 (a trade name of anionic surfactant; manufactured by Toho Chemical Co.) | 4 parts |
| Carplex # 80 (a trade name of white carbon; Shionogi Pharmaceutical Co.) | 2 parts |

The above components are homogeneously mixed and pulverized to give a wettable powder. On application, the wettable powder is diluted 500 to 2,000 times and sprayed so that the crystal toxin-containing material can be provided at 0.1-5 kg per hectare.

FORMULATION EXAMPLE 2: POWDER

| | |
|---|---|
| the crystal toxin-containing material according to the present invention | 3.0 parts |
| Clay | 95 parts |
| diisopropyl phosphate | 1.5 parts |
| Carplex # 80 | 0.5 parts |

The above components are homogeneously mixed and pulverized to give a powder. On application, the powder is sprayed so that the crystal toxin containing material can be provided at 0.1-5 kg per hectare.

FORMULATION EXAMPLE 3: FLOWABLE AGENT

| | |
|---|---|
| the crystal toxin-containing material according to the present invention | 35 parts |
| Lunox 1000C (a trade name of anionic surfactant; manufactured by Toho Chemical Co.) | 0.5 parts |
| Solpol 3353 (a trade name of nonionic surfactant; manufactured by Toho Chemical Co.) | 10 parts |
| 1% Xanthene gum aqueous solution | 20 parts |
| Water | 34.5 parts |

The above components except the crystal toxin-containing material are homogeneously dissolved, mixed with the crystal toxin-containing material, well stirred and wet-pulverized by a sand mill to give a flowable powder. On application, the flowable powder is diluted 50 to 2,000 times and sprayed so that the crystal toxin-containing material can be provided at 0.1-5 kg per hectare.

It is well known that the toxic protein produced by Bt is encoded by the gene (CP gene) contained in a huge plasmid of the strain. Accordingly, the gene coding for the insecticidal crystal toxin can be cloned, introduced into bacteria such as *E. coli* and *Pseudomonos* or target plants to be protected from lepidopterous insect pests by means of a known genetic engineering technology so as to exterminate said pests.

An example of the method for the protection of a plant from damage caused by the lepidopterous insect pests is to treat or spray a plant with the above agent diluted with, for example, water. The active component of the agent is a toxic δ-endotoxin. The agent according to the present invention may comprise the toxic δ- endotoxin per se or the strains producing it. Thus, it is not generally necessary to isolate the toxic δ-endotoxin from the strains.

Another example of the method is to prepare a plant susceptible to said damage so that it can produce in vivo the toxic δ-endotoxin. The preparation may be carried out by cloning the genes coding for the δ-endotoxin from the novel strains No.145, No.116 and No.161, ligating them with a suitable promoter which can permit an expression of the same genes in the plant, for example, CaMV35S promoter, transforming the plant in a known manner such as Ti plasmid and electroporation.

The insect pests which can be eradicated by the present method are, for example, Lepidoptera such as *Mamestra brassicae* comprising *Spodoptera litura* and *Spodoptera exigua*, *Plutella xylostella*, *Cnaphalocrocis medinalis*, *Chilo suppressalis*, *Parnara guttata*, *Pieris rapae crucivora*, *Monema flavescens*, *Papilio machaon hippocrates* and Diptera such as *Aedes aegipti*, *Culex pipiens pallens*, *Aedes albopictus* and *Anopheles hyrcanus sinensis*.

The present method can protect a wide variety of plants such as vegetables like *Brassica oleracea* var. *capitata*, fruit vegetables like a cauliflower, citrus fruits, defoliation fruits and a flowering tree as well as trees in non-crop land such as a plantation, park and forest.

EXAMPLE

Example 1

Isolation of Bt var. kurstaki No.145, No.116 and No.161 strains:

One gram of each soil sample obtained in Hokkaido area of Japan (Memuro area for No.145, Dounan area for No.116 and Moshiri area for No.661) was taken into an Erlenmeyer flask. To the flask was added 10 ml of a sterilized distilled water and shaked for 30 min. and then allowed to stand still. A supernatant liquid (2 ml) was collected and heated at 98° C. for 10 min. The resulting solution was diluted × 10 and × 100 respectively. Each of the diluted solution (1 ml) was incubated in an usual nutrient agar medium (meat extract 0.3%, peptone 0 3% and agar 1.5%, pH 7.0) on a 9 cm-Petri dish at 30° C. for 24–48 hours. The resulting colony was inoculated in an usual slant medium and incubated at 30° C. for 4–6 days. After a discriminating staining of an endospore and crystal, production of the crystal protein was detected by a phase contrast microscope (× 1,500 by means of an oil-immersion lens). The crystal protein was usually in a bipyramidal form.

A crystal-positive colony was streak ameared on an usual nutrient agar plate medium and incubated at 30° C. for 3 days to obtain a pure culture product. The discriminating staining was repeated to confirm the presence of the crystal and to check the purity thereof. The purified colony was transplanted in an agar slant medium and stored.

Example 2

Purification of the crystal toxic protein:

The strains according to the present invention were inoculated in the usual nutrient agar medium and incubated at 30° C. After a suitable period of time, a part of the incubated strains was collected and checked about the production of the crystal protein by the phase contrast microscope (× 1,500). Tris-HCl buffer (50 mM) was added to the plate medium to collect the strains, which were then centrifuged to recover a mixture pellet of the strains and crystal. In order to remove contaminants and spores which were further eluted, the following steps were carried out according to the method described in Protein, Nucleotide and Enzyme; 29, 444-454, 1984; Keiji Yamamoto. The pellet was mixed with 1 M saline and the resulting suspension was shaked hard to foam. After removal of the foam containing many floating endospores on the surface of the suspension, the suspension was again centrifuged and the supernatant was discarded. These serial procedures were repeated three times. The resulting pellet was then washed with a sterile distilled water, centrifuged, suspended with a small amount of sterile water and subjected to Percoll treatment to isolate the crystal toxin (Toshihiko Iizuka, Chemistry and Biology 27, 287–302, 1989).

Example 3

Examination of a digestion pattern of the crystal toxic protein by trypsin:

The crystal toxic protein obtained in EXAMPLE 2 was resolubilized with an alkaline solution, incubated with trypsin at 37° C. for a predetermined period of time and subjected to 10 % SDS-polyacrylamide gel electrophoresis to examine its phoresis pattern. As a control, the known strain HD-1 was used after it had been incubated and treated in the same manner as the strains according to the present invention.

The results are shown in FIG. 1.

Example 4

Culture of the strains:

A platinum loopful of the strains of the present invention was inoculated in 5 ml of the usual nutrient liquid medium in a test tube and incubated with a reciprocal shaker at 30° C. for 12 to 24 hours to obtain a seed culture. The seed culture was inoculated into an Erlenmeyer flask (500 ml) containing 100 ml of Potato-Dextrose medium (potato infusion 20%, dextrose 2%, pH7.0) at a final concentration of 1 % and incubated at 30° C. for 50 to 70 hours with a rotary shaker at 200 rpm. The cells, spores and crystal protein were recovered by centrifugation. The resulting pellet was mixed with a certain amount of water, subjected to ultrasonication, centrifuged and lyophilized. After being weighed and adjusted in concentration, the resulting dry product was subjected to the following insecticidal tests.

Example 5

Insecticidal test of the strains on *Spodoptera litura*:

Leaves of cabbage were impregnated for about 10 sec. with a predetermined amount of the solution of the strains prepared in EXAMPLE 4 and supplemented with a spreader, air-dried and taken into a styrol cup containing a wet filter paper. Ten larvae of *Spodoptera litura* (2 larval instars) were released within each of the cup provided with a cover having pores and incubated at 25° C. As a control, the known strain HD-1 was incubated and treated in the same manner as the strains according to EXAMPLE 4. The test was performed in a two-zone system. A mortality rate at 3 days after the release was calculated by the following equation.

Mortality rate=(the number of the died insects/the number of the released insects)×100

The results are shown in TABLE 1.

TABLE 1

| Sample | Conc. (ppm) | Mortality rate (%) |
| --- | --- | --- |
| No.145 | 500 | 100 |
|  | 100 | 100 |
|  | 10 | 66.7 |
|  | 1 | 9.0 |
| No.116 | 500 | 100 |
|  | 100 | 75 |
|  | 10 | 20 |
|  | 1 | 0 |
| No.161 | 500 | 100 |
|  | 100 | 90 |
|  | 10 | 50 |
|  | 1 | 43.3 |
| HD-1 | 500 | 100 |
|  | 100 | 25 |
|  | 10 | 11.1 |
|  | 1 | 0 |
| Control | 0 | 0 |

Example 6

Insecticidal test of the strains on *Plutella xylostella*:

Leaves of cabbage were impregnated for about 10 sec. with a predetermined amount of the solution of the strain prepared in EXAMPLE 4 and supplemented with a spreader, air-dried and taken into a styrol cup containing a wet filter paper. Ten larvae of *Plutella xylostella* (2 larval instars) were released within each of the cup provided with a cover having pores and incubated at 25° C. As a control, the known strain HD-1 was incubated and treated in the same manner as the strain according to EXAMPLE 4. The test was performed in a two zone system. A mortality rate at 3 days after the release was calculated by the following equation.

Mortality rate=(the number of the died insects/the number of the released insects)×100

The results are shown in TABLE 2.

TABLE 2

| Sample | Conc. (ppm) | Mortality rate (%) |
| --- | --- | --- |
| No.145 | 1 | 100 |
|  | 0.1 | 100 |
|  | 0.01 | 65 |
|  | 0.001 | 20 |
| No.116 | 1 | 100 |
|  | 0.1 | 100 |
|  | 0.01 | 90 |
|  | 0.001 | 80 |
| No.161 | 1 | 100 |
|  | 0.1 | 100 |
|  | 0.01 | 66.6 |
|  | 0.001 | 20 |
| HD-1 | 1 | 100 |
|  | 0.1 | 57.5 |
|  | 0.01 | 33.3 |
|  | 0.001 | 0 |
| Control | 0 | 0 |

Example 7

Insecticidal test of the strains on *Spodoptera exigua*:

Leaves of cabbage were impregnated for about 10 sec. with a predetermined amount of the solution of the strain prepared in EXAMPLE 4 and supplemented with a spreader, air-dried and taken into a styrol cup containing a wet filter paper. Ten larvae of *Spodoptera exigua* (2 larval instars) were released within each of the cup provided with a cover having pores and incubated at 25° C. As a control, the known strain HD-1 was incubated and treated in the same manner as the strain according to EXAMPLE 4. The test was performed in a two-zone system. A mortality rate at 3 days after the release was calculated by the following equation.

Mortality rate=(the number of the died insects/the number of the released insects)×100

The results are shown in TABLE 3.

TABLE 3

| Sample | Conc. (ppm) | Mortality rate (%) |
| --- | --- | --- |
| No.145 | 500 | 100 |
|  | 100 | 100 |
|  | 10 | 60 |
|  | 1 | 18.1 |
| No.116 | 500 | 90 |
|  | 100 | 80 |
|  | 10 | 33.3 |
|  | 1 | 0 |
| No.161 | 500 | 100 |
|  | 100 | 62.5 |
|  | 10 | 40 |
|  | 1 | 11.1 |
| HD-1 | 500 | 100 |
|  | 100 | 100 |
|  | 10 | 11.1 |
|  | 1 | 0 |
| Control | 0 | 0 |

Example 8

Mass-culture of the strains:

A platinum loopful of the strains of the present invention was inoculated in 10 ml of the usual nutrient liquid medium in an Erlenmeyer flask (100 ml) and incubated with a rotary shaker at 200 rpm at 30° C. for 12 to 24 hours to obtain a seed culture. The seed culture was inoculated into an Erlenmeyer flask (5000 ml) containing 1000 ml of Potato-Dextrose medium (potato infusion 20%, dextrose 2%, pH7.0) at a final concentration of 1 % and incubated at 28° C. for 3 to 5 days with a rotary shaker at 140 rpm. The cells, spores and crystal protein were recovered by centrifugation. The resulting pellet was mixed with a certain amount of water, subjected to ultrasonication, centrifuged and lyophilized. After being weighed and adjusted in concentration, the resulting dry product was subjected to the following insecticidal tests.

Example 9

Effect of the strains on larvae of *Pieris rapae crucivora* and *Mamestra brassicae*:

The solution (125 ppm) of the strains No.145 and No.161 prepared in EXAMPLE 8 and the solution (140 ppm) of a commercially available BT agent, Toarrow (a registered mark of Toagosei Chemical Industry Co., Ltd.) were supplemented with a spreader, which were then subjected to a field test on larvae of *Pieris rapae crucivora* and *Mamestra brassicae* in a cabbage farm. The tests were carried out in duplicate for 10 strains per zone.

The results are shown in TABLE 4.

TABLE 4

| | Insect pests (number/10 strains) *Pieris rapae crucivora/Mamestra brassicae* | | | | |
| --- | --- | --- | --- | --- | --- |
| | | After spray | | | |
| Sample | Before Spray | 4 days | 6 days | 8 days | 10 days |
| No.145 | 70/16 | 11/4 | 1/1 | 2/7 | 0/11 |

TABLE 4-continued

| | Insect pests (number/10 strains) Pieris rapae crucivora/Mamestra brassicae | | | | |
|---|---|---|---|---|---|
| | | After spray | | | |
| Sample | Before Spray | 4 days | 6 days | 8 days | 10 days |
| No.161 | 74/20 | 6/4 | 3/20 | 3/10 | 2/16 |
| Toarrow* | 48/140 | 11/16 | 9/75 | 5/72 | 7/72 |
| No spray | 42/64 | 32/43 | 33/102 | 83/110 | 51/86 |

*Toarrow 7% WP

Example 10

Effect of the strains on larvae of *Pieris rapae crucivora* and *Pluttela xylostella*:

The solution (100 ppm) of the strains No.145, No.116 and No.161 prepared in EXAMPLE 8 and the solution (140 ppm) of a commercially available BT agent, Toarrow (a registered mark of Toagosei Chemical Industry Co., Ltd.) were supplemented with a spreader, which were then subjected to a field test on larvae of Pieris rapae crucivora and *Pluttela xylostella* in a cabbage farm. The tests were carried out in duplicate for 24 strains per zone.

The results are shown in TABLE 5.

TABLE 5

| | Insect pests (number/10 strains) Pieris rapae crucivora/Pluttela xylostella | | |
|---|---|---|---|
| | | After spray | |
| Sample | Before spray | 4 days | 8 days |
| No.145 | 163/96 | 4/34 | 17/58 |
| No.116 | 131/69 | 5/23 | 12/42 |
| No.161 | 147/72 | 5/48 | 24/99 |
| Toarrow* | 179/77 | 17/42 | 19/79 |
| No spray | 174/108 | 161/331 | 213/311 |

*Toarrow 7% WP

Example 11

Insecticidal test of the strains on larvae of *Bombyx mori*:

The solution of the strains prepared in EXAMPLE 4 and Toarrow 7% WP were homogeneously mixed with 10 gram of an artificial feed. The resulting feed was taken in 2 to 3 cm height into a styrol cup. Ten larvae of *Bombyx mori* (3 larval instars) were released within each of the cup and incubated at 25° C. A mortality rate at 5 days after the release was calculated by the following equation.

Mortality rate = (the number of the died insects/the number of the released insects) × 100

The results are shown in TABLE 6.

TABLE 6

| Sample | Conc. (ppm) | Mortality rate (%) |
|---|---|---|
| No.145 | 100 | 20 |
| | 50 | 0 |
| | 25 | 0 |

TABLE 6-continued

| Sample | Conc. (ppm) | Mortality rate (%) |
|---|---|---|
| | 12.5 | 0 |
| | 6.25 | 0 |
| No.116 | 100 | 100 |
| | 50 | 65 |
| | 25 | 20 |
| | 12.5 | 5 |
| | 6.25 | 0 |
| No.161 | 100 | 100 |
| | 50 | 70 |
| | 25 | 20 |
| | 12.5 | 10 |
| | 6.25 | 0 |
| Toarrow 7% WP | 100 | 100 |
| | 50 | 100 |
| | 25 | 100 |
| | 12.5 | 100 |
| | 6.25 | 80 |
| Control | 0 | 0 |

Example 12

Insecticidal test of the strains on *Aedes albopictus*:

The solution of the strains prepared in EXAMPLE 4 were diluted with sterilized distilled water and taken into a deep laboratory dish. Ten larvae of *Aedes albopictus* (2 larval instars) were released within the dish and incubated at 25° C. The tests were carried out in a two-zone system. HD-1 and israelensis strains were also subjected to the test. A mortality rate at 3 days after the release was calculated by the following equation.

Mortality rate = (the number of the died insects/the number of the released insects) × 100

The results are shown in TABLE 7.

TABLE 7

| Sample | Conc. (ppb) | Mortality rate (%) |
|---|---|---|
| No.145 | 1000 | 100 |
| | 100 | 100 |
| | 10 | 30 |
| | 1 | 20 |
| No.116 | 1000 | 100 |
| | 100 | 100 |
| | 10 | 100 |
| | 1 | 20 |
| No.161 | 1000 | 100 |
| | 100 | 100 |
| | 10 | 40 |
| | 1 | 40 |
| HD-1 | 1000 | 50 |
| | 100 | 0 |
| | 10 | 0 |
| | 1 | 0 |
| israelensis | 1000 | 100 |
| | 100 | 100 |
| | 10 | 100 |
| | 1 | 30 |
| Control | 0 | 0 |

What is claimed is:

1. A biologically pure culture of *Bacillus thuringiensis* var. *kurstaki*, No. 145. FERM BP-3905.

2. A biologically pure culture of *Bacillus thuringiensis* var. *kurstaki*, No. 161. FERM BP-3906.

3. A biologically pure culture of *Bacillus thuringiensis* var. *kurstaki*, No. 116. FERM BP-3907.

* * * * *